United States Patent [19]

Golds et al.

[11] Patent Number: 5,383,905
[45] Date of Patent: Jan. 24, 1995

[54] SUTURE LOOP LOCKING DEVICE

[75] Inventors: Ellen M. Golds, Hastings-On-Hudson, N.Y.; Steven Howansky, Wilton, Conn.

[73] Assignee: United States Surgical Corporation, Norwalk, Conn.

[21] Appl. No.: 959,202

[22] Filed: Oct. 9, 1992

[51] Int. Cl.⁶ .................................. A61B 17/04
[52] U.S. Cl. ........................ 606/232; 606/151; 606/74; 24/136 L
[58] Field of Search .............. 606/151, 157, 191, 213, 606/215, 216, 218, 232, 74; 24/194, 16 PB, 30.5 P, 357, 136 L, 136 R, 115 M, 503, 30.5 S

[56] References Cited

U.S. PATENT DOCUMENTS

| 1,390,830 | 9/1921 | Snow . | |
|---|---|---|---|
| 2,916,785 | 12/1959 | Daugert . | |
| 3,570,497 | 3/1971 | Lemole . | |
| 3,879,147 | 4/1975 | Morell | 403/369 |
| 3,946,467 | 3/1976 | Lukas et al. | 24/537 |
| 3,952,377 | 4/1976 | Morell . | |
| 4,037,603 | 7/1977 | Wendorff . | |
| 4,066,368 | 1/1978 | Mastalski et al. . | |
| 4,156,574 | 5/1979 | Boden . | |
| 4,291,698 | 9/1981 | Fuchs et al. . | |
| 4,333,649 | 6/1982 | Vaughn et al. . | |
| 4,379,358 | 4/1983 | Wibrow . | |
| 4,455,717 | 6/1984 | Gray | 24/136 R |
| 4,509,233 | 4/1985 | Shaw . | |
| 4,615,532 | 10/1986 | Biller et al. . | |
| 4,738,255 | 4/1988 | Goble et al. . | |
| 4,741,330 | 5/1988 | Hayhurst . | |
| 4,782,560 | 11/1988 | Keller . | |
| 4,839,946 | 6/1989 | Murai . | |
| 4,845,814 | 7/1989 | Crook | 24/136 R |
| 4,955,913 | 9/1990 | Robinson | 606/228 |
| 5,009,663 | 4/1991 | Broomé | 602/232 |
| 5,015,023 | 5/1991 | Hall | 294/102.1 |
| 5,037,422 | 8/1991 | Hayhurst et al. | 606/72 |
| 5,046,513 | 9/1991 | Gatturna et al. | 128/898 |
| 5,074,874 | 12/1991 | Yoon et al. | 606/224 |
| 5,078,731 | 1/1992 | Hayhurst | 606/232 |
| 5,123,913 | 6/1992 | Wilk et al. | 606/232 |

FOREIGN PATENT DOCUMENTS

| 2431490 | 1/1976 | Germany | 24/136 R |
|---|---|---|---|
| 163340 | 6/1921 | United Kingdom | 24/136 R |
| 751959 | 7/1980 | U.S.S.R. | 24/136 R |

Primary Examiner—Tamara L. Graysay

[57] ABSTRACT

A device for securing a suture loop about bodily tissue includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway. The device has application in conventional and endoscopic surgical procedures including laparoscopic procedures.

19 Claims, 5 Drawing Sheets

SUTURE LOOP LOCKING DEVICE

BACKGROUND OF THE INVENTION

1. Field of the Invention

The present invention relates to surgical devices and more particularly to a suture device for securing a suture loop which is passed through or about bodily tissue. The device has particular application in endoscopic and laparoscopic surgical procedures.

2. Discussion of the Prior Art

Suturing of bodily tissue is a time consuming component of most surgical procedures including both conventional surgery and endoscopic surgery. Typically, suturing is accomplished by passing a needle through tissue and tieing the free ends of the suture together with a knot. In conventional surgery, the suturing site is exposed sufficiently to permit the surgeon to tie the suture by hand. However, in endoscopic and laparoscopic surgery, the suture ends are often tied into a knot at a location remote from the tissue site. The knot is then manipulated with an appropriate endoscopic instrument to slide the knot to the targeted tissue.

A particular objective in tieing off a suture around tissue is achieving the appropriate tension on the suture material to accommodate the particular tissue being sutured so as to control approximation, occlusion, attachment or other conditions of the tissue. However, the surgeon's ability to apply the appropriate level of tension to the suture is often inhibited, particularly in endoscopic surgery where suturing is performed with the use of an elongated endoscopic instrument, which instrument requires numerous difficult manipulations to perform the suturing procedure. Due to the difficult manipulations required, the integrity of the suture knot formed is frequently in question and the time expended to form this knot is often excessive, thus, offsetting the inherent advantages of the endoscopic and laparoscopic surgical techniques, i.e., reduced operative time and trauma to the patient.

Accordingly, it would be desirable to provide a suture device which can tie off a suture loop about tissue in an effective and efficient manner. It would also be desirable to provide a device which facilitates the surgeon's ability to control the amount of tension exerted on the suture loop. The present invention incorporates a locking device which facilitates quick knotting and tieing as needed during critical surgical procedures, which device can be utilized in both conventional and endoscopic surgery.

SUMMARY OF THE INVENTION

A device for securing a suture loop about tissue portion comprises a bead member having a longitudinal bore extending therethrough and an anchor member slidably insertable within the bore of the bead member. The anchor member defines a longitudinal passageway for reception of two end portions of a suture loop. The anchor member assumes a compressed condition upon at least partial insertion thereof within the bore of the bead member to securely wedge the suture end portions received within the passageway to retain the suture loop about tissue portion.

The anchor member includes at least two axial compressible sections which define therebetween the longitudinal passageway for reception of the two suture end portions. The axial sections are adapted to collapse radially inwardly towards a longitudinal axis defined by the anchor member when the anchor member is at least partially inserted within the bore of the bead member. The axial sections define inner wedging surfaces which engage the suture end portions when in the collapsed position.

In a preferred embodiment, the anchor member comprises four axial compressible sections which are generally quadrantal-shaped in cross-section. The wedging surfaces of the four axial compressible sections each define an arcuate recess. The arcuate recesses are configured and dimensioned to accommodate the two suture end portions of the suture loop. In an alternative preferred embodiment, the anchor member comprises first and second pairs of opposed axial sections. The wedging surfaces of the first pair are generally straight while the wedging surface of the second pair include arcuate recesses.

The axial sections may also each include at least one flange portion disposed on an outer peripheral surface thereof. The flange portions are configured and dimensioned to increase the effective outer diameter of the anchor member so as to maximize the amount of inward movement of the axial sections towards the longitudinal axis defined by the anchor member upon insertion thereof in the bore of the bead member. Preferably, the flange portions taper outwardly towards the rear end portion of the anchor member to facilitate insertion of the anchor member within the bead member. In the preferred embodiment, the axial sections each comprise a pair of flange portions.

In another alternative preferred embodiment, the device for securing a suture loop about tissue comprises a bead member having a longitudinal bore extending therethrough and an anchor member slidably insertable within the bore of the bead member. The anchor member defines a longitudinal passageway therethrough for reception of two end portions of a suture loop. The anchor member includes at least two axial compressible sections. Each axial section has an inner wedging surface to engage the suture end portions received within the longitudinal passageway. The axial sections are adapted to collapse radially inwardly towards a central longitudinal axis defined by the anchor member upon at least partial insertion of the anchor member within the bore of the bead member to securely wedge the suture end portions between the wedging surfaces of the axial sections so as to secure the suture loop about the tissue.

The present invention is also directed to a method for securing a suture about tissue. The method comprises the steps of looping a suture about tissue, sliding a bead member having a longitudinal bore extending therethrough over the two ends of the suture such that the suture ends are received within the longitudinal bore, advancing the bead member to a predetermined position adjacent the tissue portion, inserting the two suture ends within a longitudinal passageway defined in an anchor member, and advancing the anchor member along the two suture end portions and into the longitudinal bore of the bead member such that the anchor member assumes a collapsed condition whereby the suture end portions are securely wedged between inner wedging surfaces of the anchor member to retain the looped suture about the tissue.

In an alternative method, the bead member and anchor member are pre-assembled, i.e., the bead member is partially inserted within the anchor member prior to application of the device over the suture loop. Accordingly, the pre-assembled device is slid over the two suture ends and the device is advanced to a predetermined position adjacent the tissue portion. The suture loop is further tightened, if desired, by pulling on the suture ends. Thereafter, the anchor member is completely inserted within the bead member to secure the device.

BRIEF DESCRIPTION OF THE DRAWINGS

Preferred embodiments of the invention will be described hereinbelow with reference to the drawings wherein.

DETAILED DESCRIPTION OF THE PREFERRED EMBODIMENTS

Figure 1:
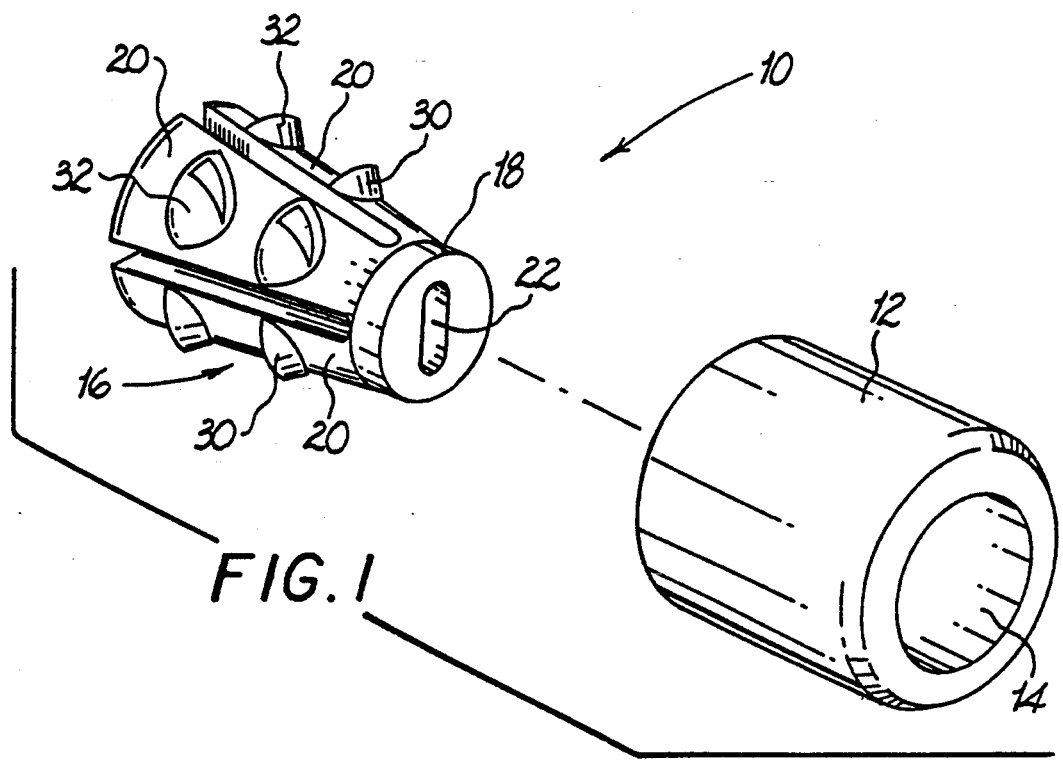
FIG. 1 is a perspective view of the suture loop locking device of the present invention illustrating the bead member and the anchor member.

Referring initially to FIG. 1, there is illustrated a perspective view of the suture loop locking device constructed according to the present invention. Locking device 10 has particular application in securing a suture loop about bodily tissue. Particularly, locking device 10 may be used to secure a suture loop about split portions of tissue for healing purposes or may be used to ligate tissue, e.g. a blood vessel. Other applications for locking device 10 may be readily appreciated by one skilled in the art such as attachment of tissue portions. Locking device 10 may be used in conjunction with endoscopic and laparoscopic surgical procedures.

Figure 2:
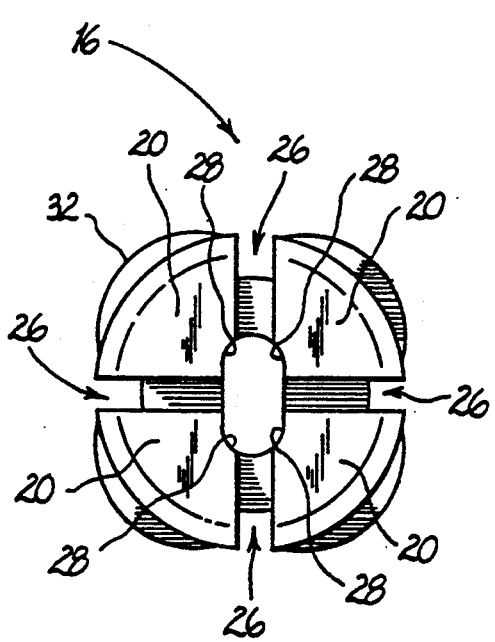
FIG. 2 is a top view of the anchor member of the locking device of FIG. 1.
Figure 3:
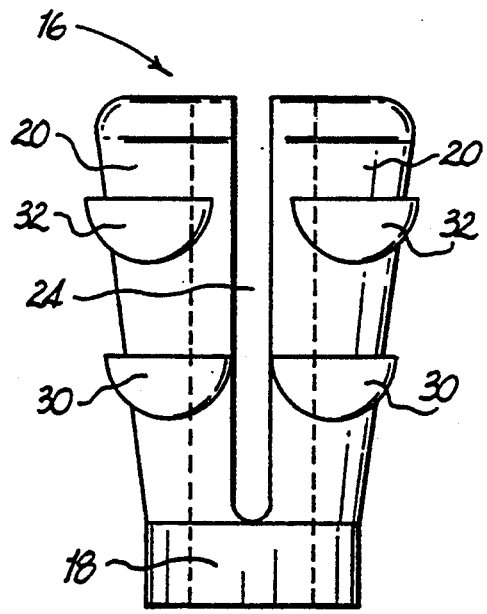
FIG. 3 is a side view of the anchor member of the locking device of FIG. 1.

Referring now to FIGS. 1-3, locking device 10 includes bead member 12 having longitudinal bore 14 and anchor member 16. Bead 12 is adapted to receive anchor 16 through bore 14. Anchor 16 is preferably generally frusto-conically shaped and includes a lower cylindrical portion 18 and four axial compressible sections 20 integrally connected to the cylindrical portion 18. Cylindrical portion 18 has a diameter slightly less than the inner diameter of bore 14 and defines a generally elongated aperture 22 to receive two end portions of a suture. Preferably, the dimension of aperture 22 approximates the dimensions of the outer diameters of the two suture end portions.

Axial sections 20 are generally quadrantal in shape in cross-section and flare outwardly to define the general frusto-conical shape of anchor 16. Axial sections 20 define a longitudinal passageway 24 through the central portion of anchor 16 through which the suture end portions received within aperture 22 may pass during suture tightening. Axial sections 20 are separated by partial longitudinal channels 26 which enable the sections to collapse radially inwardly upon insertion of anchor 16 within bore 14 of bead 12 to a strap securing position. In this position, the suture end portions are securely wedged between wedging surfaces 28 defined in the inner surfaces of axial sections 20 to secure the suture loop in a locked condition about the tissue. Wedging surfaces 28 are preferably arcuately-shaped as shown to accommodate the circular dimensions of the suture end portions. Preferably, axial sections 20 are configured to provide wedging surfaces along a substantial axial length of anchor 16. Such configuration will increase the surface area of the suture portion engaged by anchor 16, and, accordingly, will provide a more effective wedging action.

Each axial section 20 includes a pair of outwardly extending flange portions 30, 32 on its outer peripheral surface. Flange portions 30, 32 are correspondingly dimensioned and positioned to increase the effective outer diameter of the frusto-conically shaped anchor 16 so as to maximize the inward movement of axial sections 20 towards the central axis defined by the anchor during insertion thereof in bead 12, thus increasing the wedging action on the suture end portions. Flange portions 30, 32 slope outwardly away from cylindrical portion 18 to facilitate introduction of anchor 16 within bore 14. Anchor 16 and flange portions 30, 32 are advantageously dimensioned such that the suture end portions may advance through the anchor when the anchor is partially inserted within bead 12, i.e., when flange portions 30 are received within the bead.

The components of bead 12 and anchor 16 may be fabricated from catgut and from synthetic absorbable materials including polymers or copolymers of glycolide, lactide, trimethylene carbonate, dioxanone, caprolactone or blends thereof or nonabsorbable fibers including polycarbonate, polyesters, polyethylene, polyamides, polyvinyl chlorides, polypropylenes, polytetrafluoroethylene, polysulfones, acrylics and polypropylene. It is also within the scope of the present invention for device 10 to be fabricated from a combination of such absorbable and nonabsorbable materials. Preferably, device 10 is advantageously dimensioned so that it may be used in minimally invasive surgical techniques, i.e., endoscopic and laparoscopic surgery.

Further understanding of locking device 10 of the present invention will be readily appreciated from the following description of the application of same about split portions of tissue for healing purposes.

Figure 4:
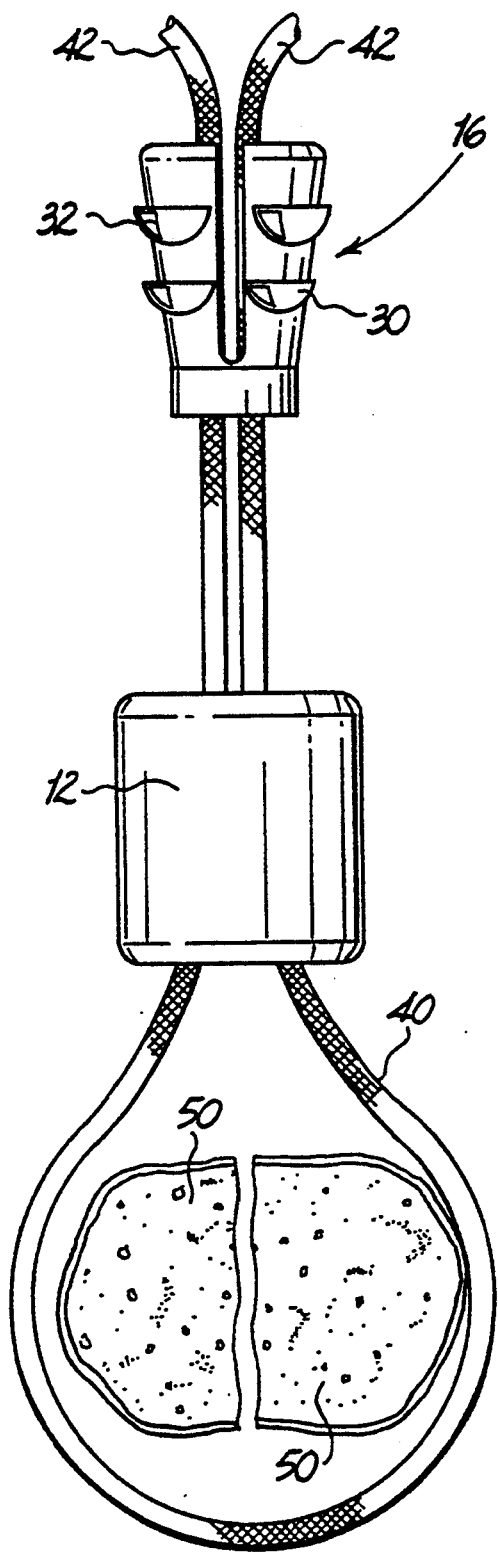
FIGS. 4-6 are side views of the locking device of FIG. 1 illustrating the sequence of steps for applying the locking device to secure a suture loop about tissue in accordance with a preferred method of the present invention.
Figure 5:
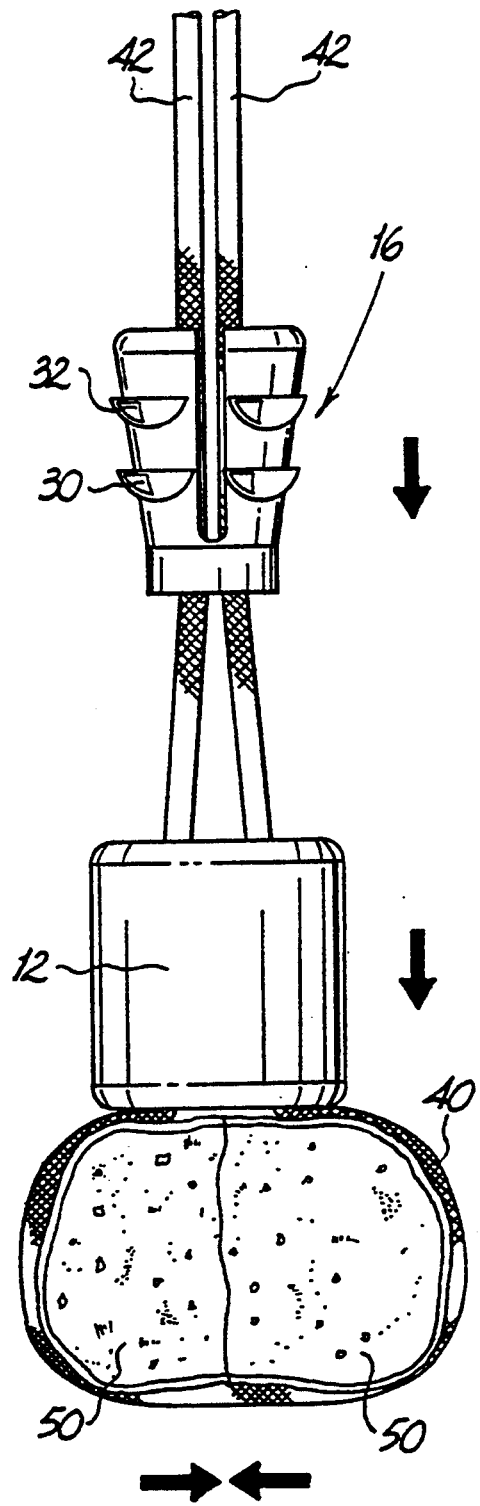
Figure 6:
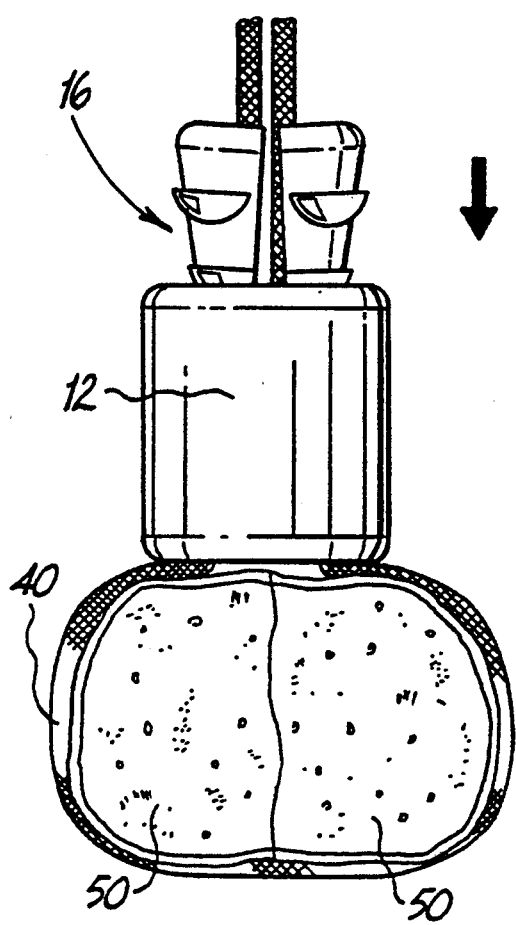

Referring initially to FIG. 4, there is illustrated a suture 40 looped about tissue portions 50, 50, with suture end portions 42, 42 inserted through longitudinal bore 14 of bead 12 and through aperture 22 defined in cylindrical portion 18 of anchor 16. Referring now to FIG. 5, bead 12 is advanced towards tissue portions 50, 50 until the bead is at a desired position adjacent the tissue portions. Suture ends 42, 42 are pulled in a tensioning direction through passageway 24 to tighten suture 40 about tissue portions 50, 50 to a predetermined desired tension. In this procedure, the suture loop is tightened such that the tissue portions are in an adjacent compressed relation. While maintaining a firm grip on suture ends 42, 42, anchor 16 is advanced in the direction indicated by the arrow towards bead 12 until the anchor is partially received within the bore as shown in FIG. 6. The suture may be further tightened or loosened about tissue portions 50, 50 if desired since anchor 16 is not completely secured within bead 12. In particular, anchor 16 is particularly dimensioned such that the suture end portions 42, 42 are capable of sliding through the anchor with slight resistance when the first set of flanges 30 is received within bore 16 of bead 14.

Figure 7:
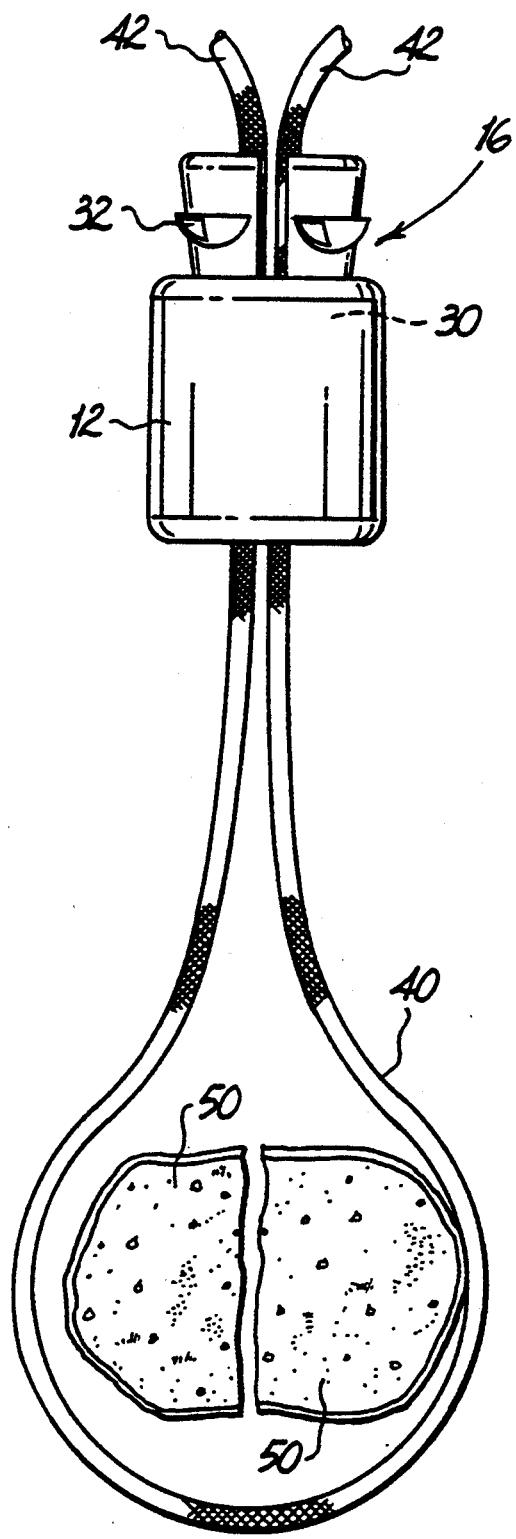
FIGS. 7-8 are side views illustrating an alternative method for applying the locking device of the present invention wherein the locking device is in a preassembled condition prior to application thereof to the suture loop.
Figure 8:
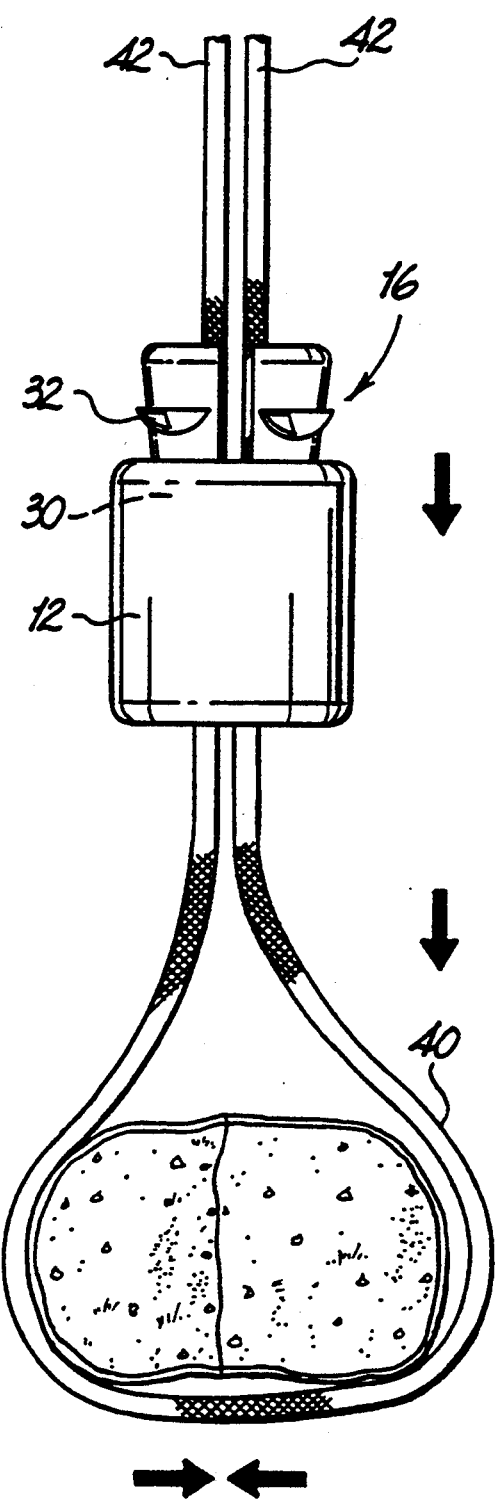

In an alternative preferred method, device 10 is partially assembled prior to application to the suture 40. In particular, anchor 16 is partially inserted within bore 14 of bead 12 such that flanges 30 are disposed within the bead as shown in FIG. 7. In accordance with this method, bead 12 and partially inserted anchor 16 are positioned over suture end portions 42, 42 and advanced along the end portions towards tissue portions 50, 50 as shown in FIG. 8 to the desired position adjacent the tissue portions (shown in FIG. 6). The suture 40 may be further tightened about tissue portions 50, 50 if desired since the wedging action provided by flanges 30 is not sufficient to completely secure anchor 16 within bead 12.

Figure 9:
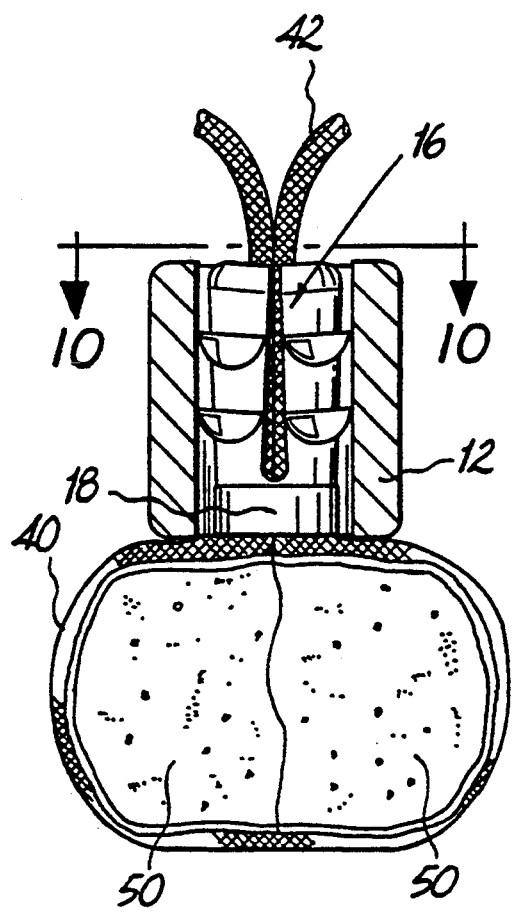
FIG. 9 is a side-sectional view of the locking device in a secured position.
Figure 10:
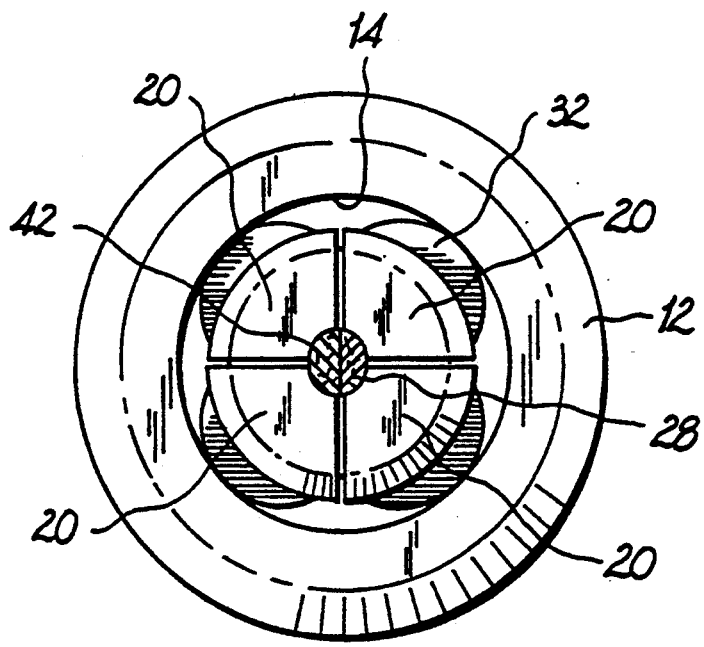
FIG. 10 is a cross-sectional view taken along the lines 10—10 of FIG. 9 illustrating the anchor member completely inserted within the bead member to securely wedge the suture end portions received within the anchor member.

Once the device is in the desired position shown in FIG. 6, by either of the afore-described methods, anchor 16 is forced completely within bore 14 of bead 12 to collapse axial sections 20 radially inwardly about the two suture portions ends as illustrated in FIG. 9. In this position, the suture portions are securely wedged between arcuate wedging surfaces 28 of axial sections 20 to secure the looped suture 40 about tissue portions 50, 50 and to sustain this looped configuration during healing of the tissue. FIG. 10 illustrates in cross-section the wedging action of wedging surfaces 28 on the two suture portions.

Locking device 10 may be applied to and secured about the tissue by hand or with appropriate grasping instrumentation. In endoscopic and laparoscopic surgery, the device 10 may be applied with endoscopic forceps or the like which are introduced through appropriately positioned trocar sleeves. The device is particularly useful in such surgical procedures because it can be readily applied to the suture loop and secured thereto with minimal difficulty and in less time as compared to conventional techniques for securing suture. The device also provides a means to control the amount of tension in the suture loop during final securement of the device. In particular, the surgeon can maintain or adjust the amount of tension exerted on the strap by pulling on the suture ends while simultaneously driving the anchor member 16 into the bead 12 to finally secure the device.

Figure 11:
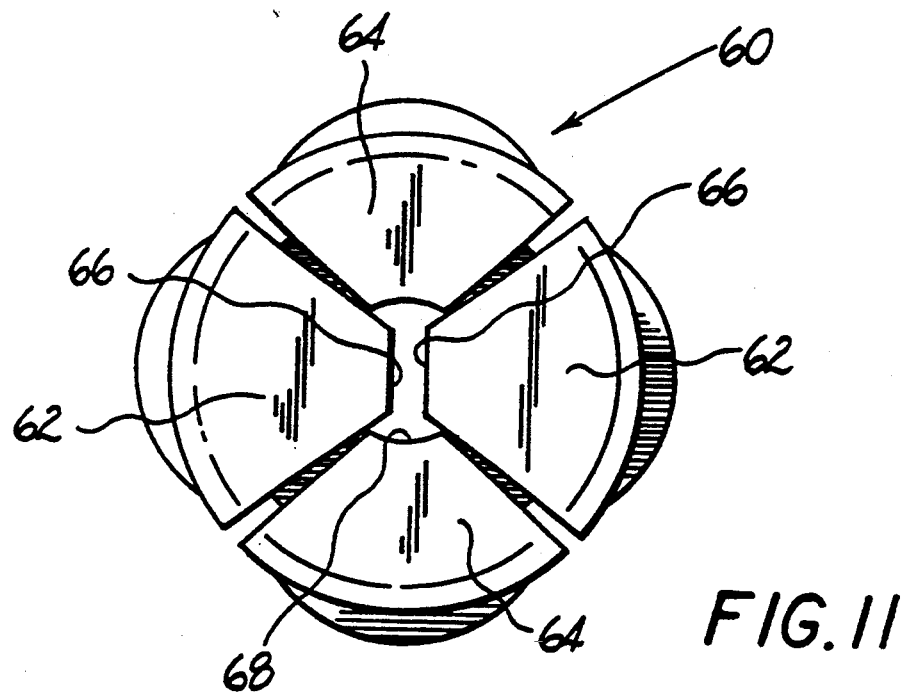
FIG. 11 is a top view of an alternative embodiment of the anchor member of FIG. 1.
Figure 12:
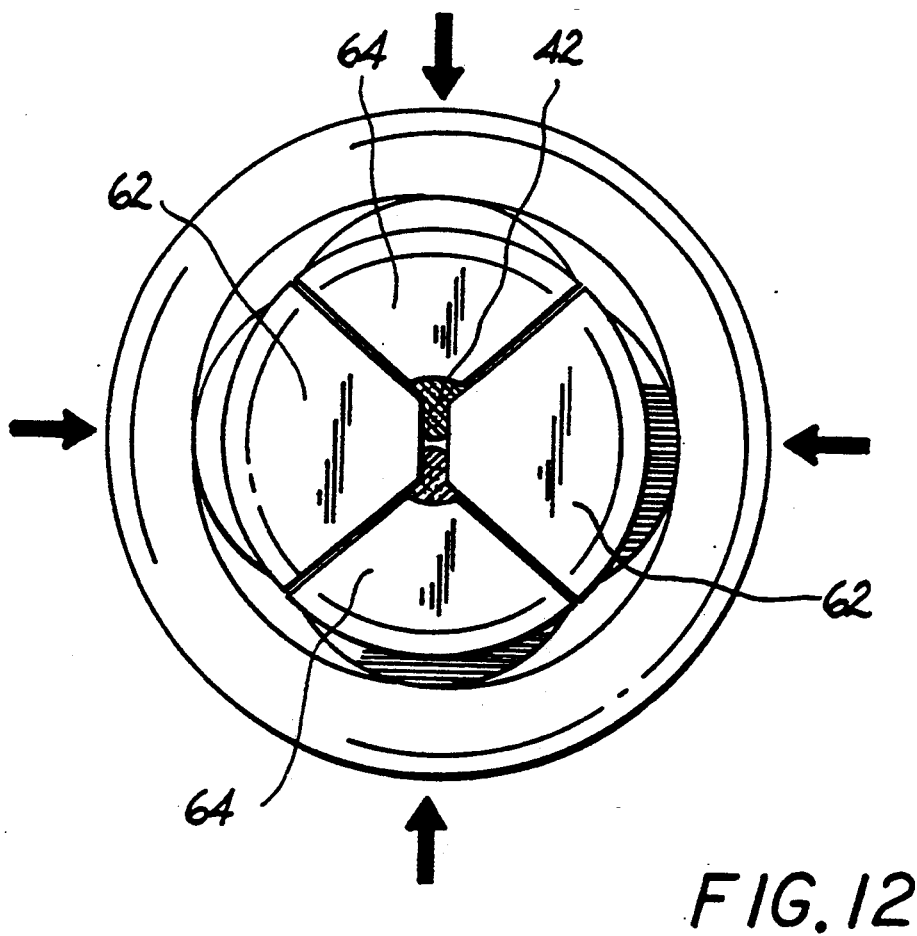
FIG. 12 is a top view of the anchor member of FIG. 11 completely inserted within the bead member to securely wedge the suture end portions received within the anchor member.

Referring now to FIGS. 11–12, an alternative embodiment of the anchor member of the present invention is illustrated. Anchor 60 includes first and second opposed pairs of axial compressible sections 62, 64. The first pair defines generally straight wedging surfaces 66 which engage a substantial surface portion of each of the suture ends 42 when in the secured wedged position shown in FIG. 10. The second pair 64 defines wedging surfaces 68 having arcuate portions which are dimensioned to receive suture material overflow caused by the wedging action of the first pair of wedging surfaces 66. In all other respects, this embodiment is similar to the embodiment of FIG. 1.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A device for securing a suture loop about bodily tissue, which comprises:

a bead member having a longitudinal bore extending therethrough, said longitudinal bore defining a cross sectional dimension which is substantially constant throughout the length of said longitudinal bore; and an anchor member slidably insertable within said bore of said bead member and defining a longitudinal passageway therethrough for reception of two end portions of a suture looped about tissue, said anchor member comprising a base portion and at least two axial compressible sections integrally connected at respective first end portions thereof to said base portion, each said at least two axial sections tapering generally outwardly towards a second end portion thereof relative to a longitudinal axis defined by said anchor member, said at least two axial sections adapted to collapse radially inwardly towards said longitudinal axis defined by said anchor member upon at least partial insertion of said anchor member within said bore of said bead member to securely wedge the suture end portions received within said passageway of said anchor member to secure the suture looped about tissue.

2. The suture device according to claim 1 wherein the crosssectional dimension of said longitudinal bore is substantially circular.

3. A suture device for securing a suture loop about a tissue portion, which comprises:

an individual suture adapted to be looped about tissue;

a bead member having a longitudinal bore extending therethrough wherein two end portions of said looped suture are passed through said longitudinal bore; and an anchor member comprising first and second pairs of opposed axial sections, said first and second pairs of axial sections including inner wedging surfaces and defining therebetween a longitudinal passageway for reception of said two end portions of said looped suture, said first and second pairs of axial sections being adapted to collapse radially inwardly towards a longitudinal axis defined by said anchor member when said anchor member is at least partially inserted within said bore of said bead member to securely wedge said suture end portions received within said passageway between said wedging surfaces thereof to retain said looped suture about the tissue, wherein said wedging surfaces of said first pair of said axial sections is generally straight and said wedging surfaces of said second pair of axial sections include arcuate recesses.

4. A method for securing a suture about tissue, comprising the steps of:

looping a suture about tissue;

sliding a bead member having a longitudinal bore extending therethrough over the two ends of the suture such that the suture ends are received within said longitudinal bore;

advancing said bead member to a predetermined position adjacent the tissue portion;

inserting the two suture ends within a longitudinal passageway defined in an anchor member; and advancing said anchor member along the two suture end portions and into said longitudinal bore of said bead member such that said anchor member assumes a collapsed condition whereby the suture end portions are securely wedged between inner wedging surfaces of said anchor member to retain the looped suture about the tissue.

5. A method for securing a suture about tissue, comprising the steps of:

looping a suture about tissue;

sliding a locking device including a bead member defining a longitudinal bore therethrough and an anchor member partially inserted within said bore of said bead member over the two ends of the suture such that the suture ends are received within a longitudinal passageway defined in said anchor member;

advancing said bead member and said partially inserted anchor member along the two suture end portions to a predetermined position adjacent the tissue portion; and driving said anchor member within said bead member such that said anchor member is fully received therewithin to collapse the anchor member and securely wedge the suture end portions between inner wedging surfaces of said anchor member to retain the looped suture about the tissue.

6. A suture device for securing a suture loop about tissue portion, which comprises:

an individual suture adapted to be looped about tissue;

a bead member having a longitudinal bore extending therethrough wherein two end portions of said looped suture are passed through said longitudinal bore; and an anchor member comprising at least two axial compressible sections, said at least two axial sections defining therebetween a longitudinal passageway for reception of said two end portions of said looped suture, said at least two axial sections including inner wedging surfaces and being adapted to collapse radially inwardly towards a longitudinal axis defined by said anchor member when said anchor member is at least partially inserted within said bore of said bead member to securely wedge said suture end portions received within said passageway to retain said looped suture about the tissue, said at least two axial sections each including at least one flange portion disposed on an outer peripheral surface thereof, said flange portions correspondingly dimensioned and positioned to increase the effective outer diameter of said anchor member so as to maximize the amount of inward movement of said axial sections towards said longitudinal axis defined by said anchor member upon insertion thereof in said bore of said bead member.

7. The device according to claim 6, wherein said flange portions taper outwardly towards a rear end portion of said anchor member to facilitate insertion of said anchor member within said bead member.

8. The device according to claim 7, wherein said at least two axial sections each comprise a pair of said flange portions.

9. A suture device for securing a suture loop about a tissue portion, which comprises:

an individual suture adapted to be looped about tissue;

a bead member having a longitudinal bore extending therethrough wherein two end portions of said looped suture are passed through said longitudinal bore; and an anchor member comprising four axial compressible sections, each said axial compressible section defining an inner wedging surface, said four axial sections defining therebetween a longitudinal passageway for reception of said two end portions of said looped suture and being adapted to collapse radially inwardly towards a longitudinal axis defined by said anchor member when said anchor member is at least partially inserted within said bore of said bead member to securely wedge said suture end portions between said inner wedging surfaces to thereby retain said looped suture about the tissue.

10. The device according to claim 9, wherein said four axial compressible sections are generally quadrantal-shaped in cross-section.

11. The device according to claim 10, wherein said wedging surfaces of said four axial compressible sections each define an arcuate recess, said arcuate recesses configured and dimensioned to accommodate said two suture end portions of said looped suture.

12. A suturing device, which comprises:

a flexible suture adapted to be looped about bodily tissue and having first and second end portions;

a bead member having a longitudinal bore extending therethrough and dimensioned for reception of said first and second end portions of said suture thereby forming a loop about the bodily tissue;

an anchor member slidably insertable within said bore of said bead member and defining a longitudinal passageway therethrough for reception of said first and second end portions of said suture looped about tissue, said anchor member comprising a base portion and at least two axial compressible sections integrally connected at respective first end portions thereof to said base portion, each said at least two axial sections tapering generally outwardly towards a second end portion thereof relative to a longitudinal axis defined by said anchor member, said at least two axial sections adapted to collapse radially inwardly towards said longitudinal axis defined by said anchor member upon at least partial insertion of said anchor member within said bore of said bead member to selectively secure said suture loop at a desired tension about tissue.

13. The device according to claim 12, wherein said anchor member is generally frusto-conically shaped.

14. The device according to claim 13, wherein the outer diameter of at least a portion of said anchor member is greater than the diameter of said longitudinal bore of said bead member.

15. The device according to claim 12 wherein said anchor member comprises four said axial sections, and wherein said anchor member has a generally frusto-conical shape.

16. The device according to claim 12, wherein said bead member comprises nonabsorbable synthetic fibers selected from the group consisting of polycarbonate, polyesters, polyethylene, polyamides, polyvinyl chlorides, polypropylenes, polytetrafluoroethylene and polysulfones.

17. The device according to claim 12, wherein said bead member comprises bioabsorbable fibers selected from the group consisting of catgut and synthetic materials including polymers and copolymers of lactide, glycolide, dioxanone, caprolactone and trimethylene carbonate.

18. The device according to claim 12, wherein said anchor member comprises nonabsorbable synthetic fibers selected from the group consisting of polycarbonate, polyesters, polyethylene, polyamides, polyvinyl chlorides, polypropylenes, polytetrafluoroethylene and polysulfones.

19. The device according to claim 12, wherein said anchor member comprises bioabsorbable fibers selected from the group consisting of catgut and synthetic materials including polymers and copolymers of lactide, glycolide, dioxanone, caprolactone and trimethylene carbonate.

* * * * *